US008940050B2

(12) United States Patent (10) Patent No.: US 8,940,050 B2
Laurence et al. (45) Date of Patent: Jan. 27, 2015

(54) FLEXIBLE VERTEBRAL SPACER

(75) Inventors: Lawton Laurence, West Chester, PA (US); Wamis Singhatat, West Chester, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 693 days.

(21) Appl. No.: 12/760,956

(22) Filed: Apr. 15, 2010

(65) Prior Publication Data

US 2011/0106260 A1 May 5, 2011

Related U.S. Application Data

(60) Provisional application No. 61/169,453, filed on Apr. 15, 2009.

(51) Int. Cl.
*A61F 2/44* (2006.01)
*A61F 2/30* (2006.01)
*A61F 2/46* (2006.01)

(52) U.S. Cl.
CPC ....... *A61F 2/4465* (2013.01); *A61F 2250/0029* (2013.01); *A61F 2002/30629* (2013.01); *A61F 2250/0064* (2013.01); *A61F 2002/30018* (2013.01); *A61F 2002/4687* (2013.01); *A61F 2002/4415* (2013.01); *A61F 2002/30598* (2013.01); *A61F 2002/30596* (2013.01); *A61F 2002/30632* (2013.01); *A61F 2002/30634* (2013.01); *A61F 2220/0091* (2013.01); *A61F 2/4425* (2013.01); *A61F 2002/30616* (2013.01);
(Continued)

(58) Field of Classification Search
USPC ............................. 623/17.11–17.16; 606/99
See application file for complete search history.

(56) References Cited

U.S. PATENT DOCUMENTS

| 5,888,223 A * | 3/1999 | Bray, Jr. ...................... 623/17.16 |
| 6,080,158 A * | 6/2000 | Lin ................................ 606/247 |
| 2004/0093083 A1* | 5/2004 | Branch et al. ............... 623/17.11 |

(Continued)

FOREIGN PATENT DOCUMENTS

| WO | WO 2005/077288 A1 | 8/2005 |
| WO | WO 2008/016598 A2 | 2/2008 |
| WO | WO 2010/121002 | 10/2010 |

OTHER PUBLICATIONS

U.S. Appl. No. 61/169,453, filed Apr. 15, 2009, Laurence.

(Continued)

*Primary Examiner* — Andrew Yang
*Assistant Examiner* — Diana S Jones
(74) *Attorney, Agent, or Firm* — Baker & Hostetler LLP

(57) ABSTRACT

A flexible implant system for positioning a flexible spacer between adjacent vertebrae including and interbody spacer and an insertion instrument. The interbody spacer including a central axis, a lateral axis, a top surface positioned generally parallel to the central axis and a plurality of hinge sections extending generally perpendicular to the central axis. A plurality of notches making up the plurality of hinge sections adjacent the top surface that permit the interbody spacer to flex. The interbody spacer further including a groove extending along a lateral side surface, generally parallel to the central axis. An insertion instrument includes a proximal end, a distal end and a tongue extending from the proximal end to the distal end along a non-linear path. The groove slidably engages the tongue to guide the interbody spacer from the proximal end to the distal end along the non-linear path.

54 Claims, 12 Drawing Sheets

(52) U.S. Cl.
CPC ............... *A61F 2002/30471* (2013.01); *A61F 2002/30624* (2013.01); *A61F 2/4611* (2013.01)
USPC ....................................................... 623/17.16

(56) References Cited

U.S. PATENT DOCUMENTS

| | | | |
|---|---|---|---|
| 2004/0127990 A1* | 7/2004 | Bartish et al. | 623/17.11 |
| 2006/0058876 A1* | 3/2006 | McKinley | 623/17.11 |
| 2006/0247781 A1* | 11/2006 | Francis | 623/17.16 |
| 2007/0010889 A1 | 1/2007 | Francis | |
| 2008/0058933 A1* | 3/2008 | Garner et al. | 623/17.11 |
| 2008/0125865 A1* | 5/2008 | Abdelgany | 623/17.16 |
| 2009/0030423 A1* | 1/2009 | Puno | 606/99 |

OTHER PUBLICATIONS

International Patent Application No. PCT/US2010/031200: International Search Report dated Aug. 20, 2010, 16 pages.

* cited by examiner

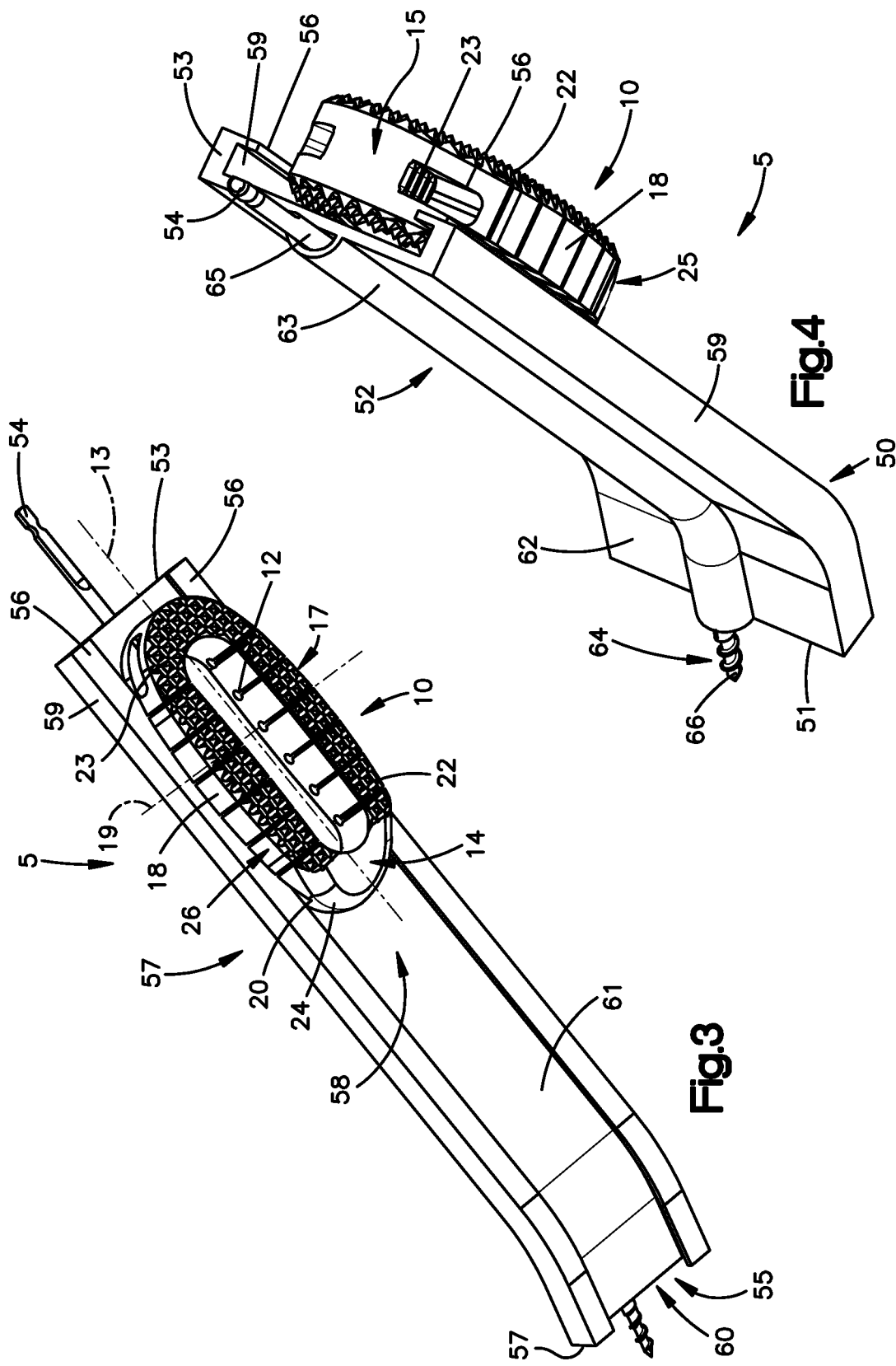

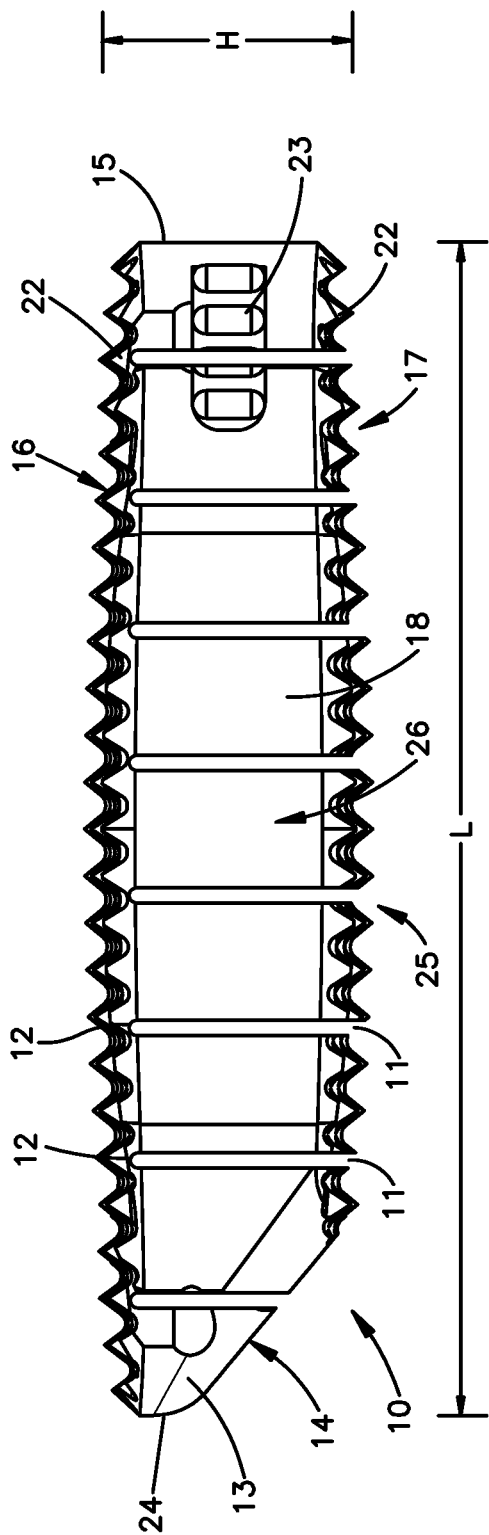
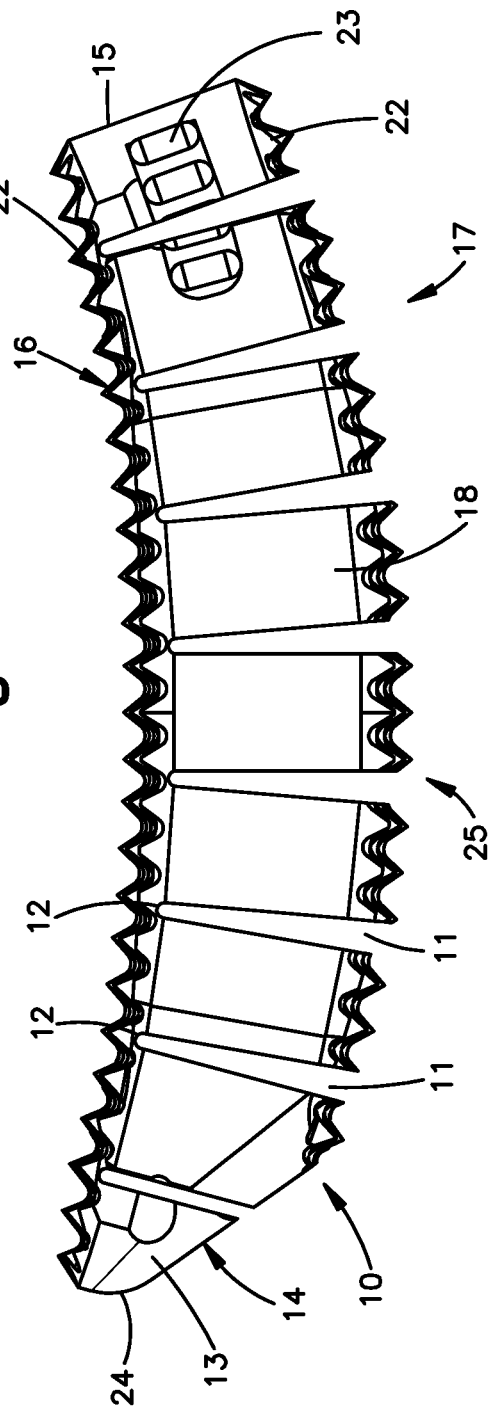
Fig.6
Fig.7

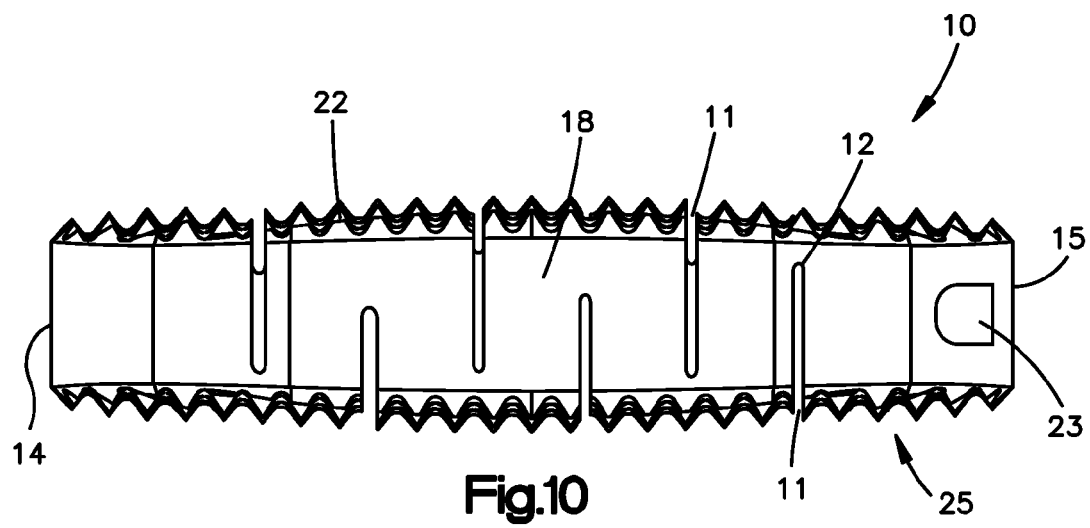
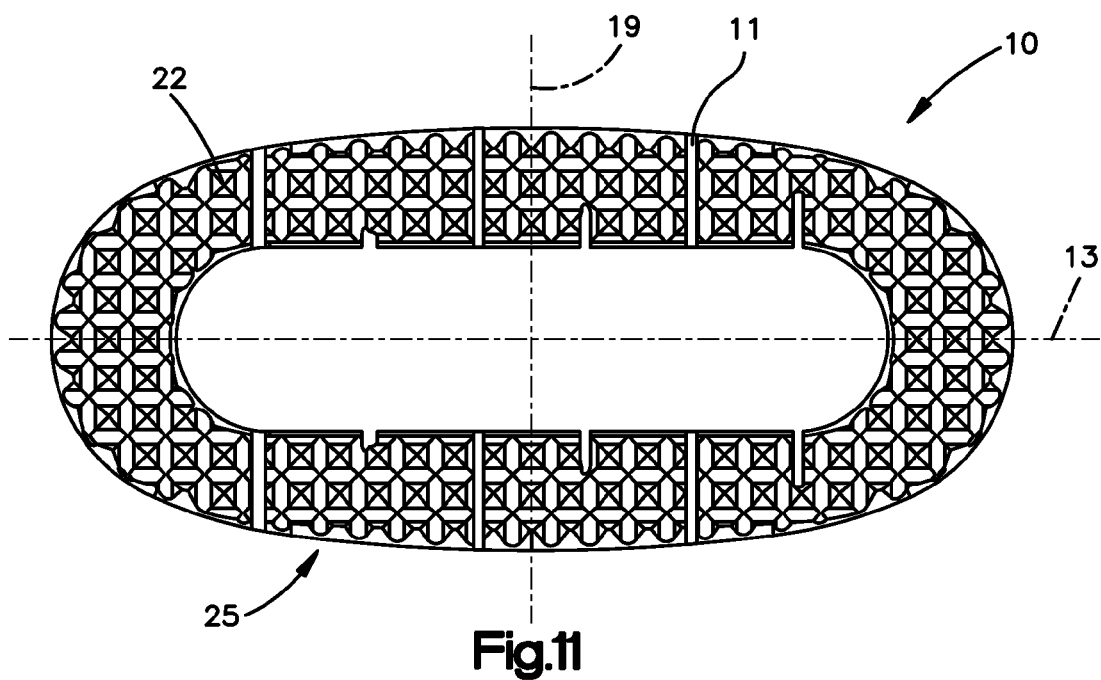

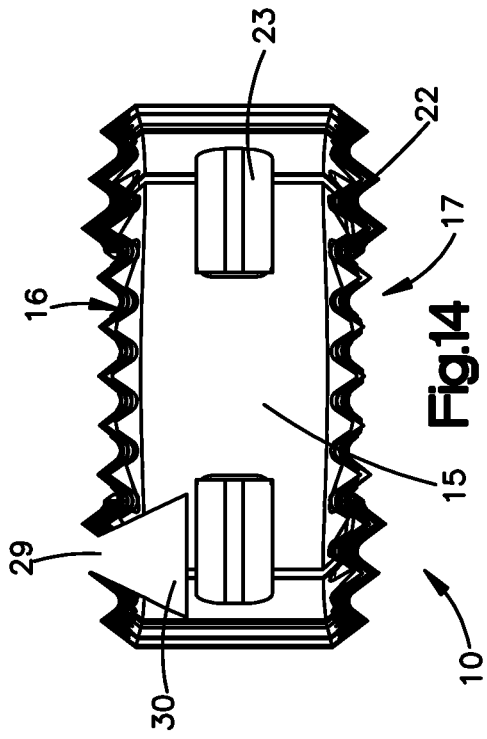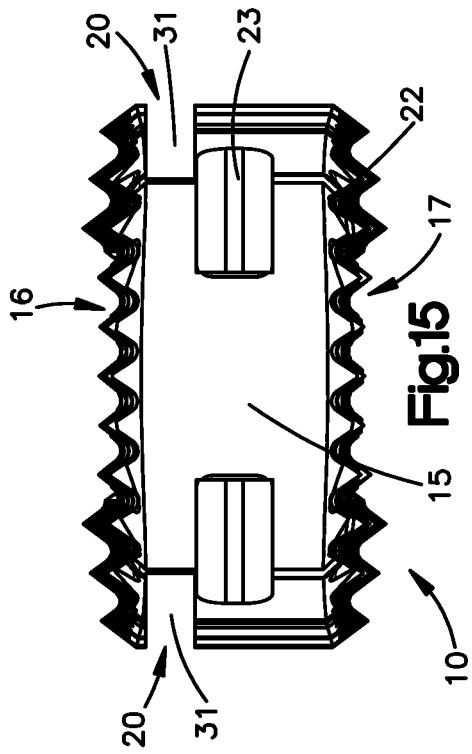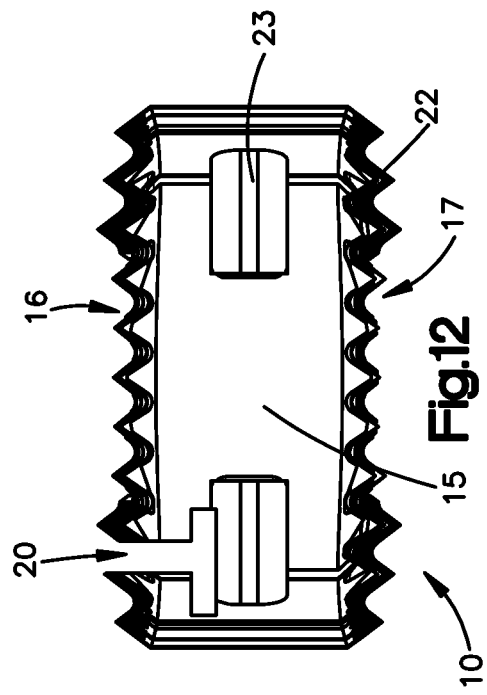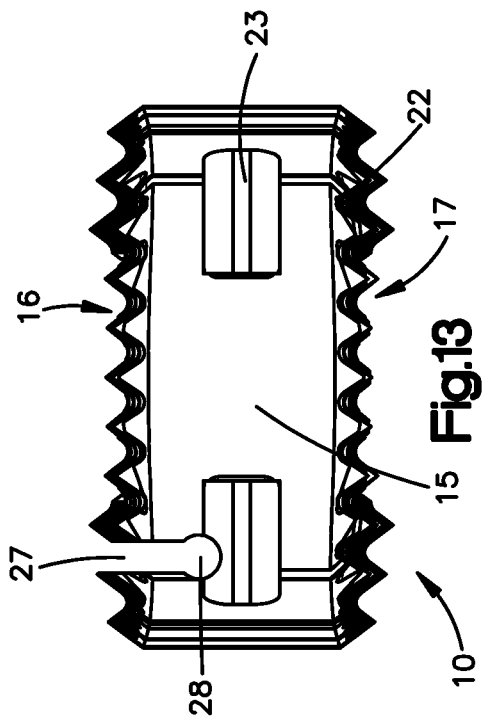

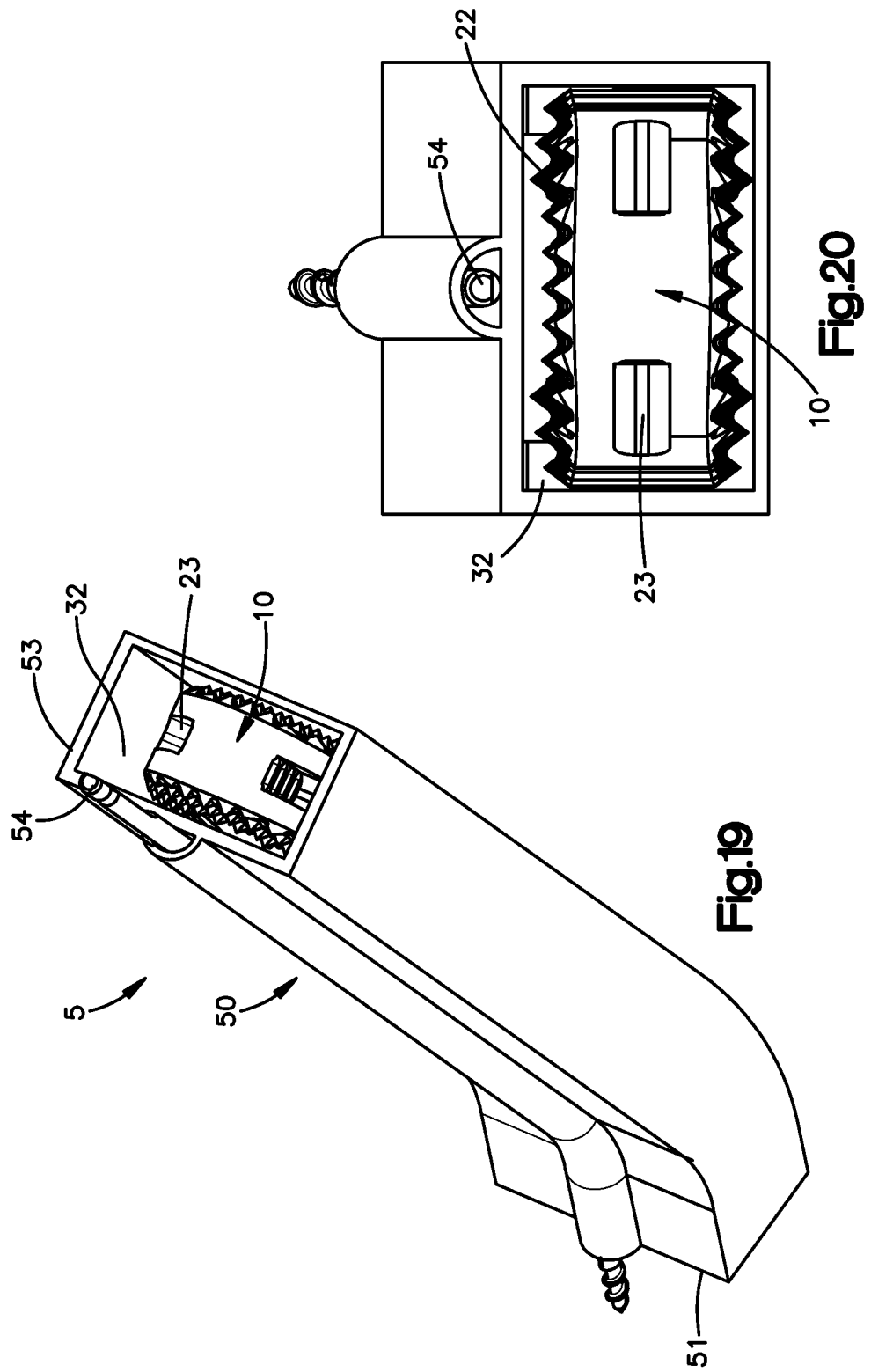

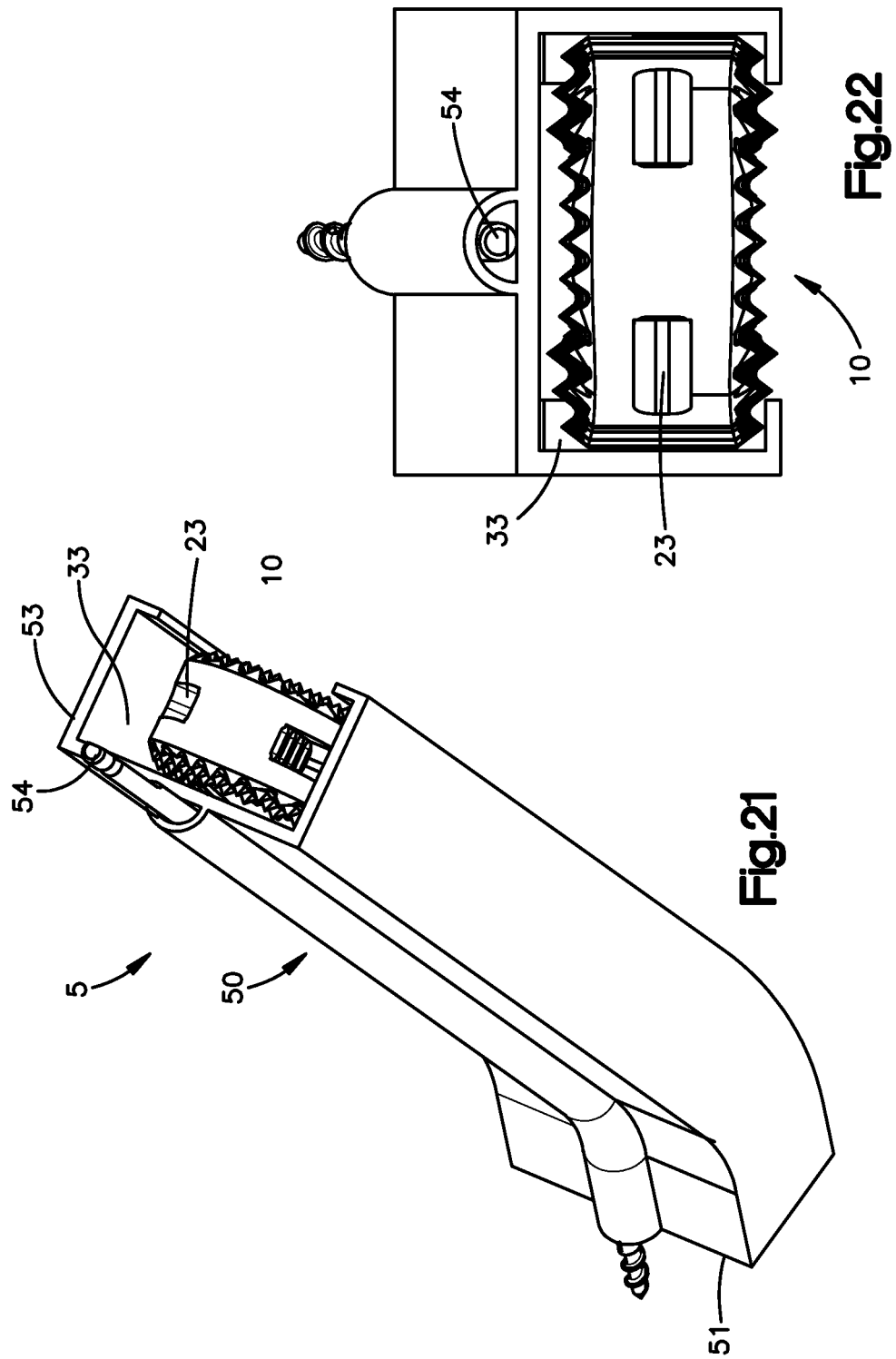

FLEXIBLE VERTEBRAL SPACER

CROSS REFERENCE TO RELATED APPLICATION

This application claims benefit to U.S. Provisional Application Ser. No. 61/169,453 filed Apr. 15, 2009, herein incorporated in its entirety by reference.

TECHNICAL FIELD

This disclosure relates generally to an interbody spacer and instrumentation, and in particular relates to a flexible spacer, instrumentation and methods for implanting the flexible spacer along a non-linear surgical path.

BACKGROUND

Human intervertbral discs generally serve two functions, they cushion and allow movement between two adjacent vertebrae. The cushioning is performed by a gel-like material, which forms the inner part of the discs. These discs are known to deteriorate with age, injury, or disease. When discs are damaged or diseased, the mobility of the subject is often impaired and great pain may result from movement. Damaged discs may also place pressure on the spinal column, causing additional pain.

To relieve the pain associated with disc injury and disease, it has been known to remove the diseased or damaged disc from the intervertebral space, and fuse or otherwise join the adjacent vertebrae that define the intervertebral space. Fusion is often desirable because it serves to fix the vertebral bodies together to prevent movement and maintain the space originally occupied by the intervertebral disc.

Interbody spacers are commonly used to promote fusion in an intervertebral disc between two vertebrae. Common surgical approaches to the disc require a linear "line-of-sight" insertion path $L_{IP}$ (See FIG. 1) that is in-plane with the disc to be fused, in order to accommodate the instruments to prepare the disc space and the linear delivery of the interbody spacer into the disc space.

Traditionally, surgical techniques involved a posterior or anterior approach through the subject to the desired intervertebral disc space. However, the posterior and anterior approaches require careful measures to be taken to avoid vascular tissues along the insertion path. Failure to do so can result in the formation of scar tissue on the vascular tissues. As a result of this and other difficulties with posterior and anterior approaches, a new lateral approach technique was developed.

The new lateral approach to the spine, which is gaining popularity for fusion procedures, allows the surgeon to gain access to the desired intervertebral disc space from the patient's lateral side. The lateral approach generally allows a more complete preparation of the disc space, including a more thorough and complete removal of the original disc material, compared to a posterior approach. A lateral approach also limits access-related surgical trauma and exposure to certain neurological, vascular and other structures while surgically accessing the disc space. Additionally, this improved access allows a larger interbody spacer to be inserted. However, a limitation of the lateral approach is that it is difficult to access the commonly-pathologic L5-S1 lumbar disc due to the patient's iliac crest obstructing the line-of-sight surgical approach. Accessing the L4-L5 space can also prove difficult using a lateral, linear (or line-of-sight) approach.

SUMMARY

A system is provided that allows a surgeon to deliver an interbody spacer into a disc space when a direct line-of-sight approach to the disc is difficult or obstructed, such as for fusing the L5-S1 lumbar disc via a lateral surgical approach. The system can include an interbody spacer and a guide rail instrument. The flexible interbody spacer (also referred to herein as a "flexible spacer", "interbody spacer" or "spacer") can be delivered along the guide rail instrument into a desired intervertebral disc space using a non-linear approach.

In accordance with one embodiment, an implant system is configured to position a flexible spacer between adjacent vertebrae. The implant system includes a flexible interbody spacer including a spacer body that defines a central axis, a lateral axis extending perpendicular to the central axis, a top surface extending substantially parallel to the central axis and a plurality of hinge sections that permit the interbody spacer to flex, the interbody spacer including a mating surface extending along a side surface generally parallel to the central axis. The implant system further includes a guide rail including a guide rail body that defines a proximal end, an opposed distal end, and a track extending between the proximal end and the distal end along a non-linear path. The engagement member is slidably engagable with the track to guide the flexible interbody spacer from the proximal end to the distal end along the non-linear path.

BRIEF DESCRIPTION OF THE DRAWINGS

The foregoing summary, as well as the following detailed description of preferred embodiments of the application, will be better understood when read in conjunction with the appended drawings. Preferred embodiments and features of the flexible implant, related instruments, and surgical methods of the present application are shown in the drawings. It should be understood, however, that the application is not limited to the precise arrangements and instrumentalities shown. In the drawings:

FIG. 3 is a bottom perspective view of the flexible implant and insertion instrument of FIG. 1, wherein the flexible implant is in the first implantation position;

FIG. 4 is a rear perspective view of the flexible implant and insertion instrument of FIG. 1, wherein the flexible implant is in the first implantation position;

FIGS. 6 and 7 are side elevation views of the flexible implant of FIG. 1 in a planar position and a flexed position, respectively;

FIGS. 10 and 11 are side elevation and top plan views of a flexible implant in accordance with a third preferred embodiment of the present invention; and FIGS. 12-15 are rear elevation views of a flexible implant in accordance with a fourth preferred embodiment of the present invention.

FIG. 19 is a rear perspective view of a flexible implant mounted to an insertion instrument according to another embodiment;

FIG. 20 is a rear elevation view of the flexible implant mounted to the insertion instrument of FIG. 19;

FIG. 21 is a rear perspective view of a flexible implant mounted to an insertion instrument according to another embodiment;

FIG. 22 is a rear elevation view of the flexible implant mounted to the insertion instrument of FIG. 21.

DETAILED DESCRIPTION OF ILLUSTRATIVE EMBODIMENTS

Figure 1:
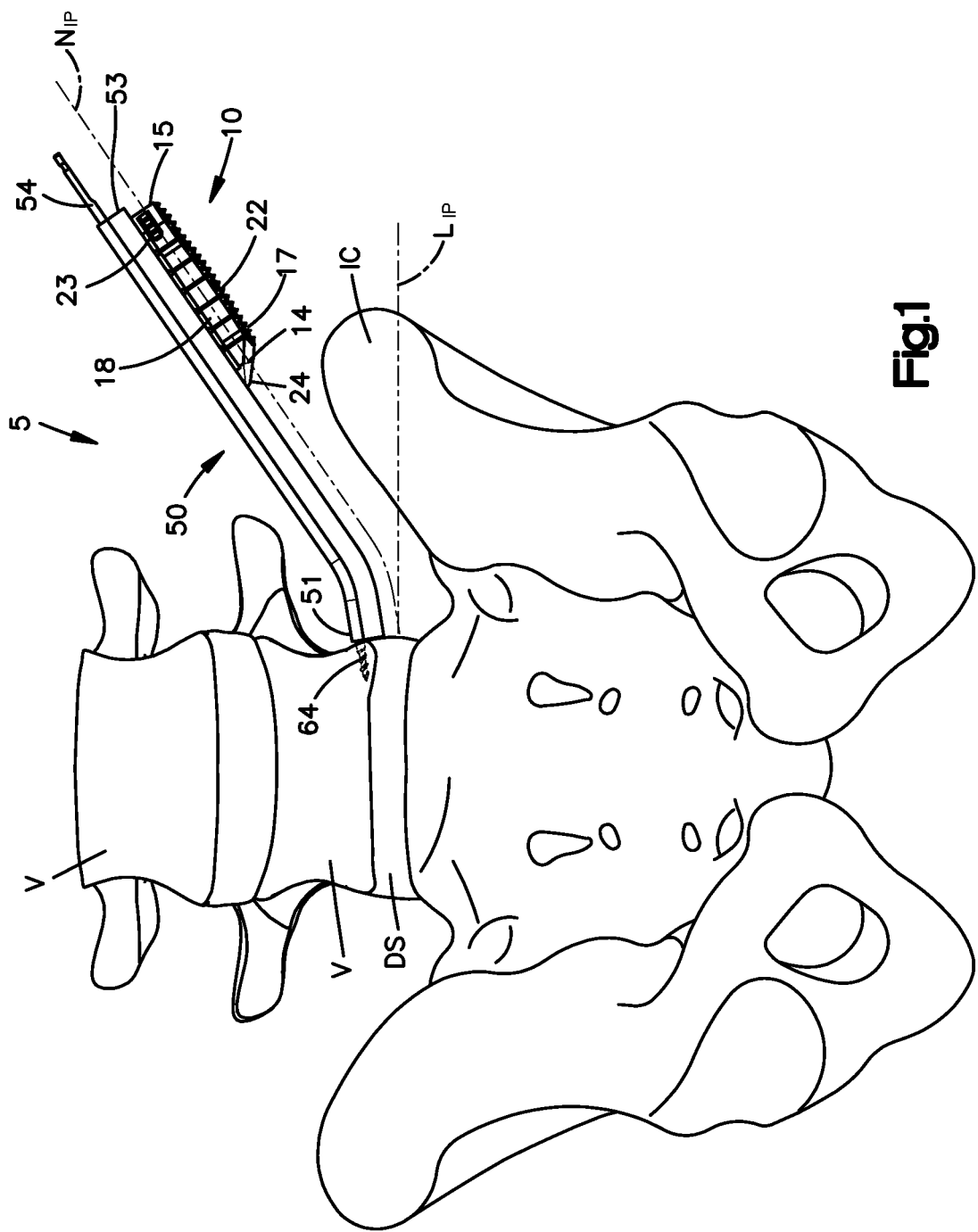
FIG. 1 is a side elevation view of a flexible implant mounted to an insertion instrument in accordance with a first preferred embodiment of the present invention, wherein the flexible implant is shown in a first implantation position and the insertion instrument is mounted to an L5 vertebra.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior", "lateral", "medial", "sagittal", "axial", "coronal" and related words and/or phrases designate preferred positions and orientations in the human body to which reference is made and are not meant to be limiting. The terminology includes the above-listed words, derivatives thereof and words of similar import.

Referring to FIG. 1, an implant system 5 includes an interbody spacer 10 and a guide rail instrument 50. The system 5 is configured to deliver the flexible interbody spacer 10 into a desired intervertebral disc space DS along a non-linear insertion path $N_{IP}$, thereby avoiding anatomical obstructions, for example, the hip and iliac crest IC of a patient. The a interbody spacer 10 can be flexible, thereby allowing the spacer 10 to deform or flex as it is delivered along a non-linear delivery path $N_{IP}$ into the disc space DS. The spacer 10 can therefore also be referred to herein as a flexible spacer that can deform or flex as it is inserted into the disc space DS. The terms "deform" and "flex" (and variants thereof) generally refer to a change in size and/or shape of the interbody spacer 10 during delivery into the disc space DS. For instance, in one embodiment, the interbody spacer 10 can change its shape so as to bend about an axis of the interbody spacer 10. In addition, the preferred interbody spacer 10 is able to withstand typical compression loads encountered in the patient's spine in an implanted position.

Figure 2:
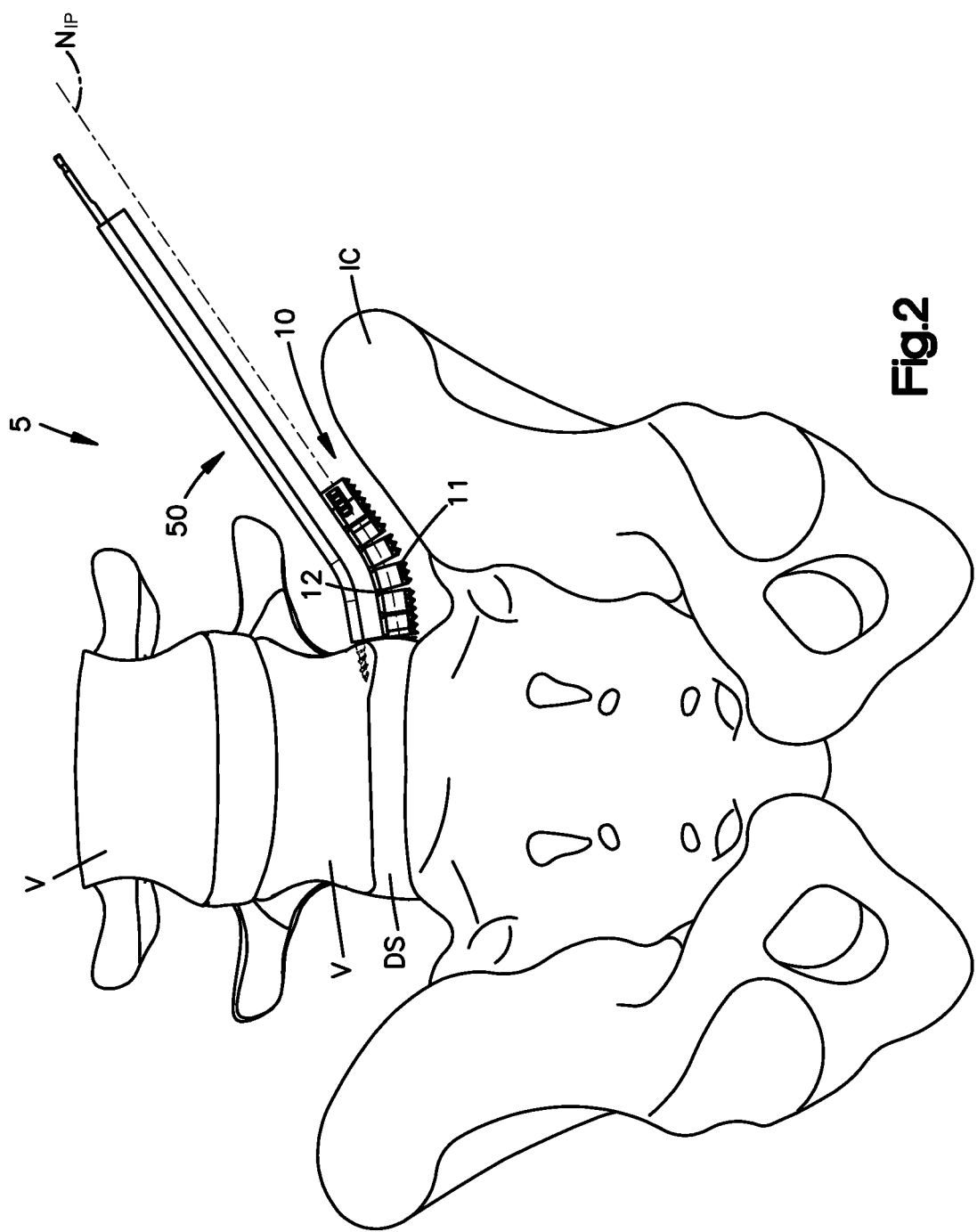
FIG. 2 is a side elevation view of the flexible implant and insertion instrument of FIG. 1, wherein the flexible implant is in a second implantation position and the insertion instrument is mounted to the L5 vertebra.

The guide rail instrument 50 includes a guide rail instrument body 57 that defines a proximal end 53 and an opposed distal end 51. The distal end 51 is configured to engage a vertebra V that at least partially defines a target intervertebral disc space DS in which the spacer 10 is to be implanted. The guide rail instrument includes an engagement mechanism 52 that extends from the distal end 51 of the guide rail body 57 and is configured to temporarily secure the guide rail instrument 50 to the adjacent vertebrae V which will aid a surgeon in proper placement of the flexible spacer 10 in the disc space DS. As shown in FIG. 2, the spacer 10 is configured to translate along the guide rail in a direction from the proximal end 53 toward the distal end 51 so as to be inserted into the disc space DS.

Referring also to FIGS. 3-4, the guide rail body 57 defines a non-linear track 55 that extends along the non-linear insertion path, and is thus configured to movably support the spacer 10 such that the spacer 10 can move along the track from a region outside the disc space DS, and in fact outside the iliac crest IC, into the disc space DS. In accordance with the illustrated embodiment, the track 55 includes a base member 58 extending between the proximal end 53 and the distal end 51, and a pair of opposed side walls 59 extending out from the base member 58. The guide rail body 57 further includes a pair of lips 56 that extend inward toward each other from the respective side walls 59. The side walls 59 and the lips 56 can be continuous or discontinuous along the length of the guide rail body 57. Thus, the track 55 is illustrated as a channel 60 disposed between the side walls 59 and lips 56, and extending between the proximal end 53 to the distal end 51. It should be appreciated that the side walls 59 can extend down or posteriorly from the base member 58 so as to align the track 55 with the disc space DS when the guide rail body 57 is secured to the superior vertebra that defines the disc space DS. Alternatively, the side walls 59 can extend up or superiorly from the base member 58 so as to align the track 55 with the disc space DS when the guide rail body 57 is secured to the inferior vertebra that defines the disc space DS. In an alternative embodiment, guide rail body 57 is not secured to a vertebra V and is instead held in place manually.

The base member 58 defines a first inner surface 61 that faces the track 55, and a second outer surface 62 that faces away from the track 55. The engagement mechanism 52 includes an elongate bushing 63 connected to the outer surface 62, and extending between the proximal end 53 and the distal end 51. An engagement member 64 is disposed in the bushing 63, and defines a drive mechanism 54 that extends proximally with respect to the proximal end of the engagement member 64. A drive body 65 is disposed between the drive mechanism 54 and the engagement member 64. The engagement member 64 is shown as a threaded screw 66 configured to be driven into an external surface (such as a lateral surface) of the target vertebra V, though it should be appreciated that suitable removable fasteners (such as, but not limited to: nails, anchors, pins, etc.) would be appropriate and are also contemplated.

The drive mechanism 54 is operatively connected to the engagement member 64 and allows a surgeon to rotate the drive body 65 and the engagement member 64 easily from a distance that is removed from the disc space DS. The drive mechanism 54 is shown as a flattened semi-circular handle but other shapes would be appropriate and accomplish the same result. Drive mechanism 54 could have a separate or incorporated handle to assist a surgeon in the engagement of the engagement mechanism 52. It should be appreciated that the engagement mechanism 52 could include any number of bushings 63 and engagement members 64 as desired. Alternatively, the guide rail instrument 50 can be constructed as devoid of an engagement mechanism 52.

Figure 5:
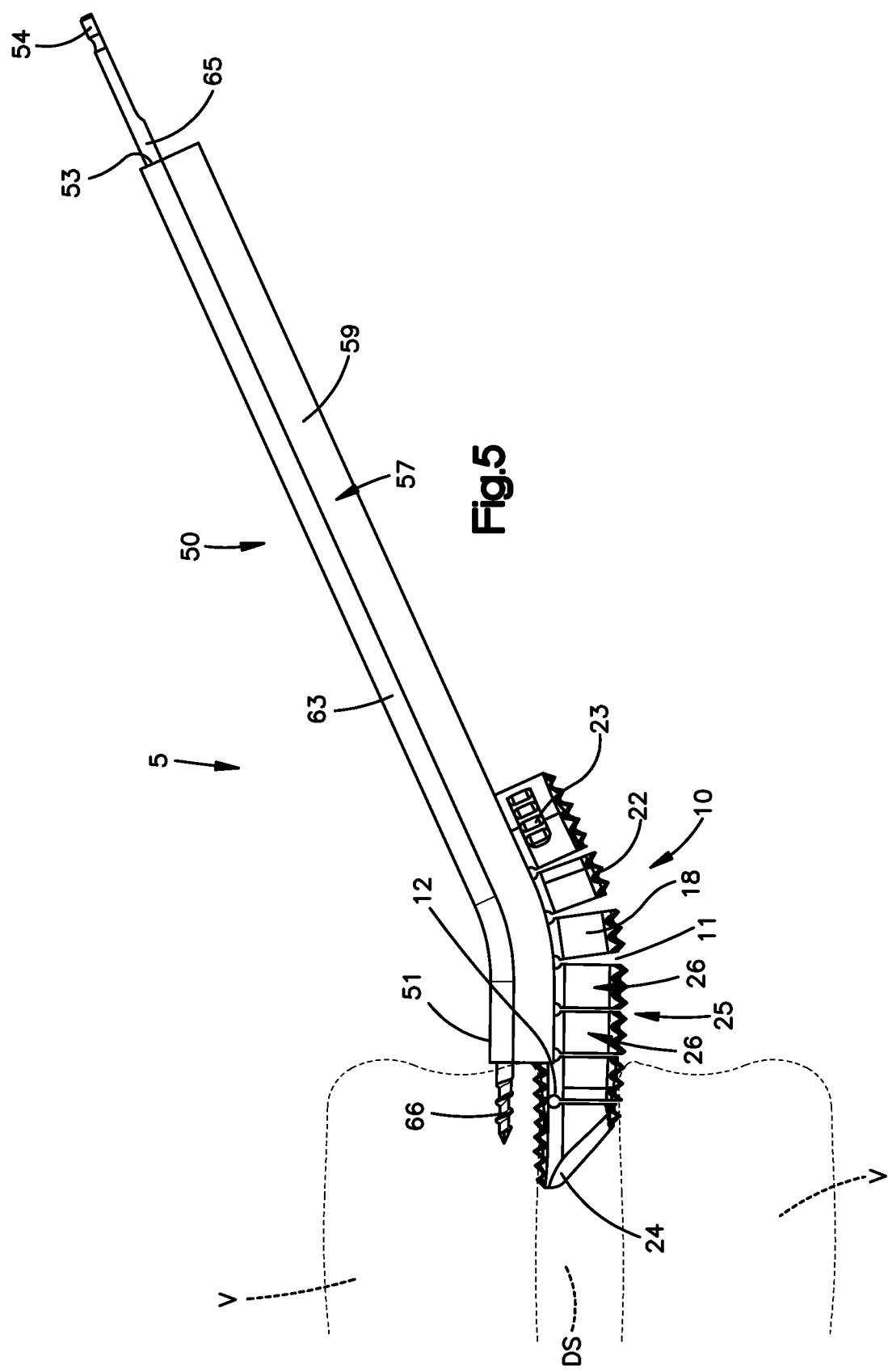
FIG. 5 is a side elevation view of the flexible implant and insertion instrument of FIG. 1, wherein the flexible implant is positioned slightly off of a distal end of the insertion instrument in a third implantation position.

In FIG. 1, the flexible spacer 10 is shown engaged with the guide rail instrument 50 in a first position prior to delivery along the non-linear insertion $N_{IP}$ path to the disc space DS. Referring to FIG. 2 flexible spacer 10 is shown at a second position along the non-linear insertion path entering the desired intervertebral disc space DS. The flexible spacer 10 is shown flexing at hinge sections 12 (See FIG. 2). FIG. 5 illustrates the flexible spacer 10 sliding off of the distal end 51 of the insertion instrument 50 into the disc space DS.

The flexible spacer 10 can be constructed of any number of implantable materials suitable for implantation into the disc space DS, including but not limited to polyether-ether-ketone (PEEK), porous PEEK, titanium, titanium alloys, metal alloys, foamed metal alloys, sintered metal alloys, ceramics, and sintered ceramics. The overall properties of the preferred spacers 10 are preferably such that it can flex during delivery along the non-linear path $N_{IP}$, while still being structurally rigid in the implanted position within the disc space DS, in order to resist physiologic loads and facilitate fusion.

Referring to FIGS. 1-7, the spacer 10 includes a spacer body 25 that defines a front or distal end 14 and an opposed back or proximal end 15 separated from each other along a central axis 13. The spacer 10 further includes a top surface 16 and an opposed bottom surface 17 that extend between the front end 14 and the back end 15. The top surface 16 is configured to face the inner surface 61 of the insertion instrument 50, while the bottom surface 17 is configured to face away from the inner surface 61 of the insertion instrument 50. The spacer body 25 defines a length L along the central axis 13 that is measured from the front end 14 to the back end 15.

The spacer body 25 includes a plurality of body segments 26 spaced along the length L of the spacer 10, and a corresponding a plurality of hinge sections 12 connected between adjacent body segments 26, so as to impart deformability and flexibility onto the spacer 10. In particular, the spacer 10 is configured to flex and/or deform about hinge sections 12. The hinge sections 12 can be defined by notches 11 that extend into the spacer body 25 along a direction that is perpendicular to the central axis 13 when the spacer 10 is orientated substantially planar. The notches 11 can extend into a top surface 16 or bottom surface 17 of the spacer 10, but are not so limited.

Figure 8:
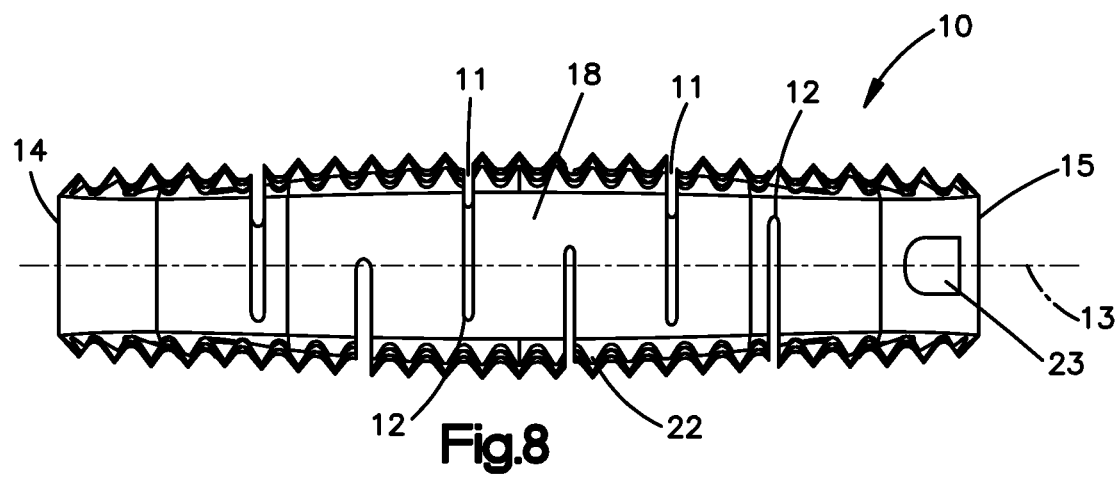
FIGS. 8 and 9 are side elevation and top perspective views of a flexible implant in accordance with a second preferred embodiment of the present invention.
Figure 9:
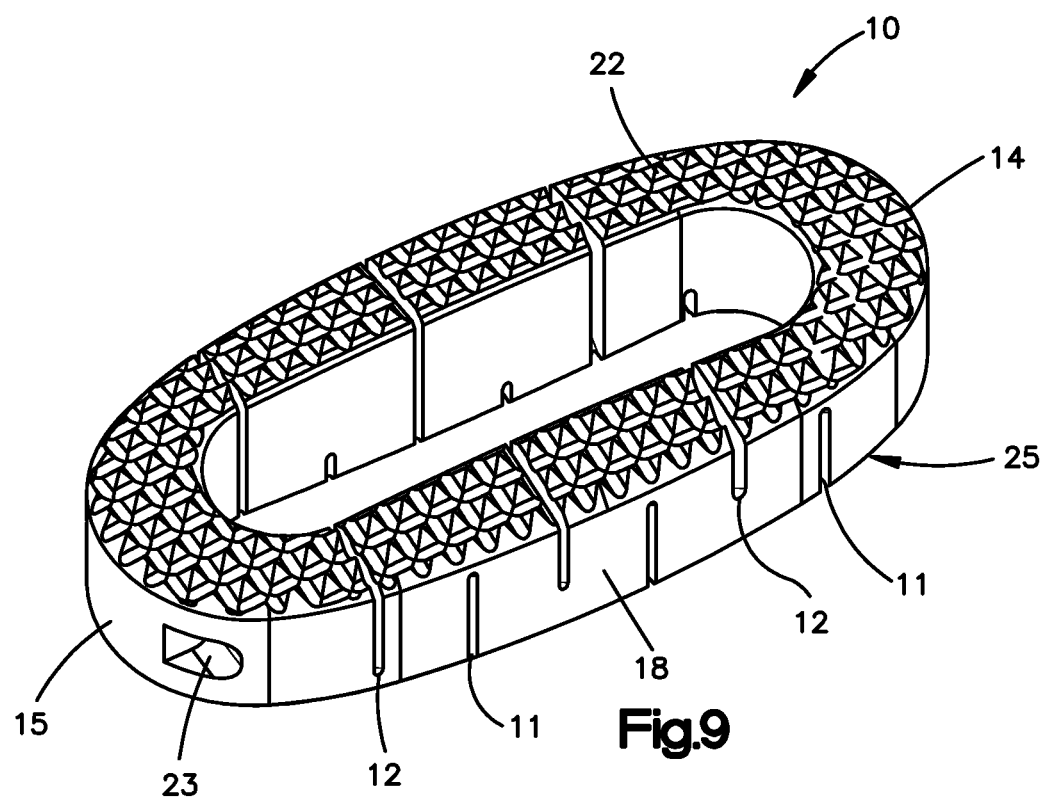

In one embodiment, the notches 11 are positioned along the length of the spacer 10 extending into the spacer body 25 from the bottom surface 17 toward the top surface 16 as shown in FIGS. 6 and 7. In another embodiment, the notches 11 could be located on a side surface 18 of the spacer 10 to allow the spacer 10 to flex laterally. Alternatively, as shown in FIG. 8, the notches 11 could be located proximate both top surface 16 and bottom surface 17 of the spacer 10 in alternating order, such the spacer 10 could flex superiorly or inferiorly. Further, the notches 11 could be oriented in any number of angles around a central axis 13 of the spacer 10, such as a helical configuration (FIG. 10 and FIG. 11) or an alternating forty-five degree)(45°) or alternatively angled configuration (FIG. 9) to allow the spacer 10 to deform about more than one degree of freedom, such as flexing along and rotating around the central axis 13 of the spacer 10. Additional degrees of freedom may be advantageous in allowing the surgeon to deliver the spacer 10 into the disc space DS without the insertion instrument 50 having to be precisely aligned to a specific orientation relative to a plane of the disc space DS. The hinge sections 12 of the spacer 10 preferably promote flexing and bending of the spacer 10 about a lateral axis 19 (See FIG. 3) to accommodate insertion of the spacer 10 along the non-linear path $N_{IP}$ shown in FIG. 1 for insertion into the disc space DS between L5 and S1 and extending superior to the patient's iliac crest IC. Lateral axis 19 is defined between the opposing side surfaces 18 along a line perpendicular to the central axis 13 and parallel to the plane of top surface 16 and bottom surface 17.

Figure 16A:
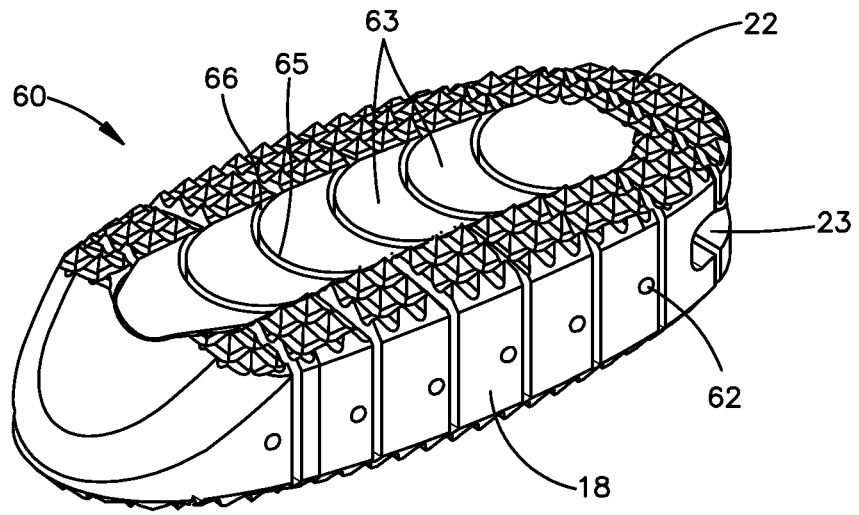
FIG. 16A is a side perspective view of a flexible implant in accordance with a fifth preferred embodiment of the present invention.
Figure 16B:
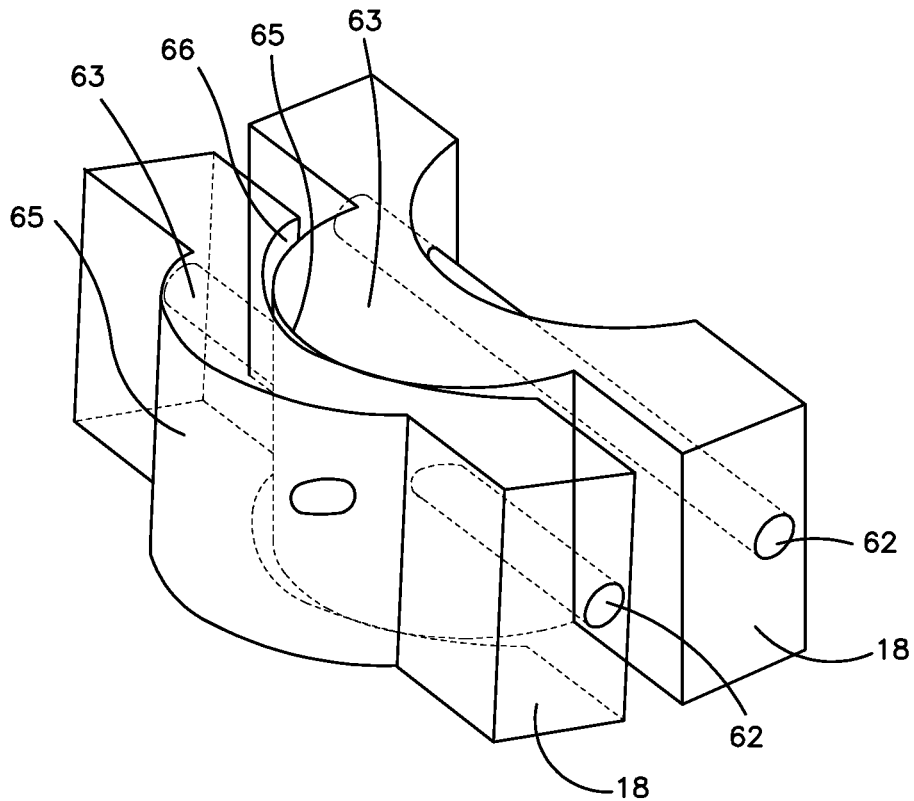
FIG. 16B is an exploded cutaway view of a flexible implant in accordance with a fifth preferred embodiment of the present invention shown in a flex position.

A variety of other mechanisms and designs can be used to construct the preferred hinge sections 12, such as a pin joint 64, as shown in FIGS. 16A and 16B, whereby each pin 62 connects two segments 63 of a spacer 60 in a manner that allows for the segments to rotate around the pin 62. Two adjacent segments 63 can overlap: a projection 65 from one segment 63 fits within a corresponding recess 66 in the adjacent segment 63. Pin 62 is inserted laterally through the two adjacent segments 63 in the area where they overlap, rotatably coupling them together and forming pin joint 64. This configuration allows the segments 63 to rotate in relation to one another about a lateral axis that extends through pin 62, allowing the overall shape of spacer 60 to change. The pin joint 64 can also be designed in a manner to allow more than one degree of freedom at each joint, such as allowing for flexing along and rotation around the central axis 13 of the spacer 60. Such a configuration could be accomplished, for example, by providing clearance between the pin diameter and inner diameters of receiving holes within the spacer segment 63.

As described above, the guide rail instrument 50 defines a track 55 that allows the spacer 10 to be slidably and releasably attached to the instrument 50. The track 55 can be sized and shaped as desired so as to mate with (for example receive or be received by) a mating surface of the spacer 10. Examples of suitable spacer mating surfaces 20 are shown in FIG. 12-15 and include but are not limited to tongue-and-groove, rail-and-slot, dovetail, or any number of keyed geometries. Specifically referring to FIGS. 12-14, various spacer mating surfaces 20 are shown.

In FIG. 12, the spacer mating surface 20 is a T-shaped recess. In use, flexible spacer 10 would be slidably engaged with guide rail instrument 50 prior to being delivered to the disc space DS along the non-linear insertion path $N_{IP}$. In this embodiment, the guide rail instrument 50 would include a T-shaped projection extending from the inner surface 61 that corresponds to the T-shaped recess of spacer 10. The spacer mating surface 20 at the front end 14 of spacer 10 is slid over the track 55 at the proximal end 53 of the guide rail instrument 50. As the flexible interbody spacer 10 is delivered to the desired intervertebral disc space DS the spacer mating surface 20 at the back end 15 of spacer 10 is slid off of the corresponding guide rail track 55 at the distal end 51 of guide rail instrument 50. The operation described above is applicable to any shaped recess, including but not limited to those mentioned below.

Referring to FIG. 13, spacer mating surface 20 includes a slot 27 extending into spacer body 25 from either top surface 16 (as shown) or, alternatively, bottom surface 17. Slot 27 terminates in a tip 28 which is wider than slot 1. Tip 28 can be circular or round as shown but is not limited to any particular geometric shape as long as it is wider than slot 27.

Referring to FIG. 14, spacer mating surface 20 includes a triangular shape. Triangular mating surface 20 extends into spacer body 25 from either top surface 16 (as shown) or, alternatively, bottom surface 17. Triangular mating slot 20 has a narrow end 29 and a broad end 30. Narrow end 29 is located at the top surface 16 (or, alternatively, bottom surface 17) and broad end 30 is located within spacer body 25.

Referring to FIG. 15, an alternate embodiment of the spacer mating surface includes a tongue-and-groove mating system instead of a keyed geometry. Spacer body 25 includes cutouts (or grooves) 31 that extend into spacer body 25 from each of the opposing sides of side surface 25. These cutouts 31 are shown as rectangular in FIG. 15, but they can have any shape that corresponds to lips (or tongues) 56 included on guide rail instrument 50. The delivery process is similar to the one described above in reference to the T-shaped recess. This engagement is also depicted clearly in FIGS. 3 and 4.

Alternatively, the flexible spacer 10 delivery can be achieved without a specifically defined mating geometry by utilizing a delivery instrument with a lumen (or cannula) or partial lumen formed to fully or partially enclose the spacer 10 in a slidable configuration, such that the delivery instrument can deliver the spacer 10 into the disc space in a non-linear path $N_{IP}$ or approach. Referring to FIGS. 19 and 20, a lumen 32 can be provided as a hollow opening in the guide rail instrument body 57 which is tube shaped. The lumen 32 extends from proximal end 53 all through guide rail instrument body 57 to distal end 51. The lumen 32 is sized and shaped to correspond to the size and shape of interbody spacer 10. The corresponding shape of the lumen 37 to the interbody spacer 10 allows interbody spacer 10 to fit inside the lumen 37 and be delivered along a non-linear insertion path $N_{IP}$ to the target disc space DS enclosed within the guide rail instrument body 57 throughout the delivery.

Referring to FIGS. 21 and 22, a partial lumen 33 can be provided as a hollow opening in the guide rail instrument body 57 which is C-shaped. The partial lumen 33 extends from proximal end 53 all through guide rail instrument body 57 to distal end 51. The partial lumen 33 is sized and shaped to correspond to the size and shape of interbody spacer 10. The corresponding shape of the lumen 37 to the interbody spacer 10 allows interbody spacer 10 to fit inside the lumen 37 and be delivered along a non-linear insertion path $N_{IP}$ to the target disc space DS enclosed within the guide rail instrument body 57 throughout the delivery.

The preferred non-linear delivery instrument 50 can also act as a tissue retractor and preferably includes a fastener or other engagement mechanism 52 at the distal end 51 to secure the insertion instrument 50 to one of the adjacent vertebrae V. The fastener 52 of the preferred insertion instrument 50 includes a drive mechanism 54 near the proximal end 53 that permits a user, preferably the surgeon, to manipulate the engagement mechanism 52 to drive the engagement mechanism 52 into the vertebra. The guide rail instrument 50 is not limited to incorporation of the engagement mechanism 52 at the distal end 51 to releasably engage the vertebra adjacent the disc space DS, but the fastener 52 can provide stability during delivery of the spacer 10 into the disc space DS along the non-linear insertion path $N_{IP}$.

The top surface 16 and bottom surface 17 provide respective superior and inferior endplate surfaces that can be sized to engage the corresponding vertebral endplates when the spacer 10 is inserted into the disc space DS. In one embodiment, the flexible spacer 10 includes a roughened top surface 16 and bottom surface 17. The roughened surfaces 16 and 17 can be made of a plurality of teeth 22 that allow the flexible spacer 10 to effectively engage the adjacent vertebrae V and keep the flexible spacer 10 from slipping out of place within the desired intervertebral disc space DS. The teeth 22 as shown in FIGS. 3 and 4 can be regularly spaced and all have an even height but other embodiments can include scattered teeth 22 of different heights along the top surface 16 and bottom surface 17. The spacer 10 can alternatively include roughened surfaces that do not contain any teeth 22, but rather have a textured surface or an uneven finish. Alternatively still, the flexible spacer 10 could have a smooth or substantially smooth top surface 16 and bottom surface 17. A smooth surface can be particularly useful in a temporary flexible spacer 10, also referred to as a "trial" spacer. A trial spacer 10 can be used by a surgeon to determine the appropriate size and shape for the permanent flexible interbody spacer 10. Trial spacer 10 can also be made of cheaper materials, such as, but not limited to stainless steel, because they do not remain in the body for a long time. Thus, the spacer 10 described herein can be used as a trial implant that is removed prior to implantation of a permanent implant, or it can be used as a permanent implant, or it can be used as both a trial implant and a permanent implant.

Referring again to FIGS. 3 and 4, the flexible spacer 10 may include a recess 23 extending into the back end 15. In one embodiment, the recess 23 can take the form of a cutout in the back end 15. The recess 23 is configured to engage with an insertion tool that may be used by a surgeon to push the flexible spacer 10 into place with the disc space DS. The recess 23 may have a textured surface that corresponds to that of an insertion tool or alternatively recess 23 could have a smooth surface.

The flexible spacer 10 can further include a sloped nose 24 located at the front end 14 of spacer 10. The nose 24 can slope so as to decrease the cross-sectional dimension of the spacer body 25 along a forward direction. The sloped nose 24 helps facilitate the entrance of flexible spacer 10 into the desired intervertebral disc space DS. Sloped nose 24 is preferably a tapered slope as shown in FIGS. 6 and 7. In other embodiments sloped nose 24 can be a constant slope or have a rounded or bullet shaped tip. Alternatively the front end 14 of flexible spacer 10 can be flat.

The flexible interbody spacer 10 has a height H defined by the distance between the bottom surface 17 and top surface 16 as measured along a line perpendicular to the central axis 13 and lateral axis 19 of the flexible spacer 10. The central axis 13 runs from the front end 14 to the back end 15, down the middle of flexible spacer 10 halfway between the top surface 16 and the bottom surface 17 and halfway between the opposing side surfaces 18. The height H of flexible spacer 10 preferably is constant along its length L as shown in FIGS. 6 and 7. However, the height H may also vary along the length L of flexible spacer 10. The height H may be a constant slope to compensate for an uneven disc space DS. Alternatively, height H could have various different slopes along its length or any other arrangement that a surgeon would find appropriate for filling a desired disc space DS.

Other instruments may be utilized with the preferred flexible spacers 10 and non-linear delivery instrument 50 including discectomy and endplate preparation instruments that are adapted for operating along non-linear pathways $N_{IP}$. It should be understood that these instruments may include flexible shafts to be usable in combination with the non-linear approach or path $N_{IP}$ to the disc space DS.

The spacer body 25 of flexible spacer 10 could define other cross-sectional shapes, while still incorporating the structure and features described above, such as hinges, to impart flexibility. One example of an alternate cross-sectional shape is round. Spacer body 25 having a round (as opposed to a flattened disc as shown in FIG. 12) cross sectional shape may allow for easier insertion. Additionally, spacer body 25 may include threads along its round outer top, bottom and side surfaces 16, 17, 18. A rounded, threaded cross sectional shape would allow flexible spacer 10 to be inserted into disc space DS by a rotational, axial force. Other alternate spacer body 25 cross sections include oval, hexagonal, square, and rectangular.

Figure 18:
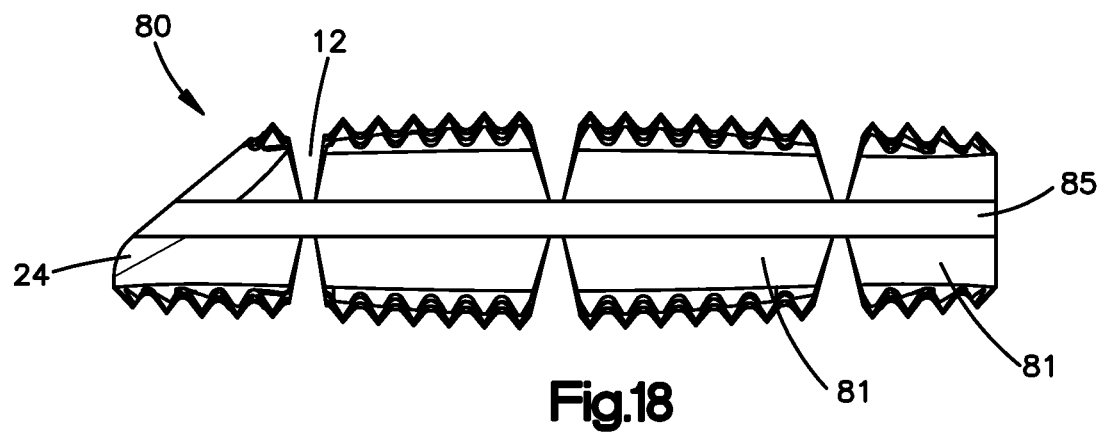
FIG. 18 is a sectional side elevation view of a flexible implant in accordance with a seventh preferred embodiment of the present invention.

The interbody spacer body 25 can be made from any material having a desired property as desired that allows for the flexibility described above. For instance, referring to FIG. 18, the spacer 10 can include a plurality of rigid segments 81 connected together along a single axis using at least one spanning member 85 inserted through each segment 81 and fixed at the ends of the assembled construct and/or fixed to each segment 81 along the length L of the construct. The spanning member 85 could be made of a suitable elastomeric material, such as silicone, polyethylene, or ultra-high molecular weight polyethylene (UHMWPE), able to allow rotation and/or bending along the central axis 13 of the construct, while allowing transmission of axial and/or torsional load required for spacer 10 implantation. Alternatively, the spanning member 85 could be made of a material suitable for being loaded under tension, such as braided cable, suture, wire, or braided high-strength fibers (e.g. UHMWPE fibers). Alternatively, each pair of rigid segments 81 could be connected by at least one separate spanning member 85 securely attached to each segment 81.

Figure 17:
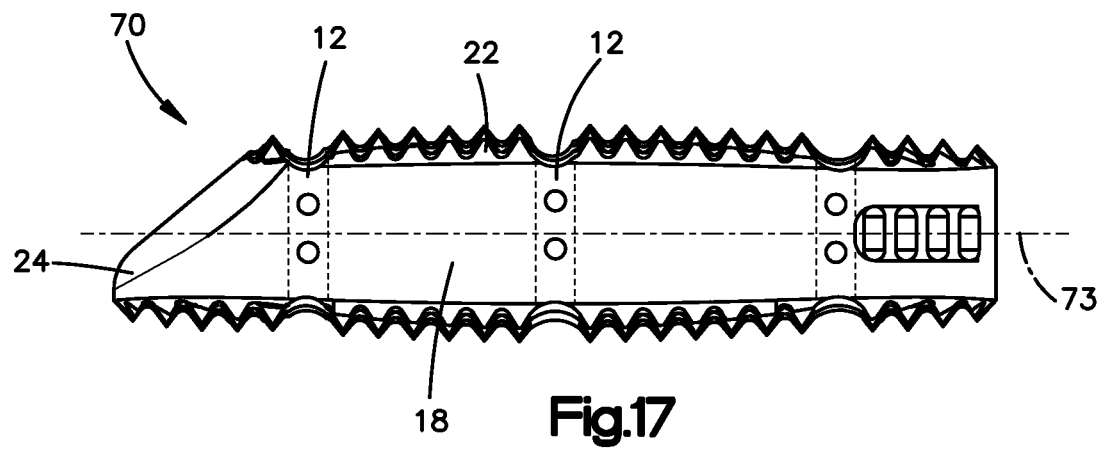
FIG. 17 is a side elevation view of a flexible implant in accordance with a sixth preferred embodiment of the present invention.

The spacer 10, the spacer 70 shown in FIG. 17, or any alternatively constructed spacer of the type described herein, or portions thereof, can further be constructed from allograft bone. The spacer 70 includes a spacer body 25 that can be machined into a desired shape. The hinge sections 12 can be demineralized (for instance by exposing the hinge sections to an acid, such as HCL, so as to remove the minerals from the hinge section 12) so as to provide flexibility at the hinge sections 12. The hinge sections 12 can be partially or fully demineralized as desired. For example, segments of the allograft bone at the hinge sections 12 could be selectively demineralized, and the hinge sections 12 could be spaced along the central axis 73 of the spacer 70. Processes to demineralize hinge sections 12 of the allograft bone may include surface masking, necking, and drilling holes in the region to be demineralized. Alternatively, as described above, an allograft spacer 80 could be comprised of a multitude of rigid segments 81, and the segments 81 could be connected by at least one spanning member 85 made of allograft tendon. Suitable allograft tendons could include, but are not limited to, Achilles tendon allografts, bone-patellar tendon-bone allografts, and fascia lata allografts.

A kit for positioning a flexible implant between adjacent vertebrae V can also be provided. In one embodiment the kit comprises the guide rail instrument 50 described above as well as a plurality of flexible interbody spacers 10 and/or spacers 70. The plurality of spacers 10 and 70 can be of various sizes and shapes. The spacers 10 and 70 can have different heights H and lengths L as well as varying arrangements of hinge sections 12 to accommodate a wide range of patients and conditions as may be needed by a surgeon. The plurality of spacers 10 can contain both temporary trial spacers and permanent spacers 10. Alternatively the kit may include a plurality of guide rail instruments 50 of various sizes, shapes, and slopes. These various guide rail instruments 50 would allow a surgeon to select the optimal approach for any given surgery. Alternatively still the kit can include a plurality of interbody spacers 10 and/or 70 as described above without a guide rail instrument.

Also provided is a method for positioning a flexible interbody spacer 10 into a desired intervertebral disc space DS between adjacent vertebrae V using a non-linear approach. Once a surgeon has gained access to the target disc space DS, the area is prepared for insertion of a flexible interbody spacer 10. This preparation can include removing the original disc material. After the disc space DS has been prepared a guide rail instrument 50 can be placed into position. Preferably the distal end 51 of the guide rail instrument 50 is engaged with an adjacent vertebrae V. This engagement preferably is performed by an engagement mechanism 52 such as a threaded screw 66 located on the distal end 51 of the guide rail instrument 50. The engagement mechanism 52 can be easily manipulated by a drive mechanism 54 located at the proximal end 53 of the guide rail instrument 50 which is operatively connected to the engagement mechanism 52. Once the guide rail instrument 50 is properly positioned, a flexible trial spacer 10 is slidably engaged with a guide rail track 55 at the proximal end 53 of the guide rail instrument 50. The flexible trial spacer 10 is then moved along a non-linear path into the desired disc space DS. Hinge sections 12 of the flexible trial spacer 10 allow the spacer 10 to flex as it travels along the non-linear insertion path $N_{IP}$. Once the trial spacer 10 is inserted it is checked to determine if it is the proper size. If a different size spacer 10 is needed the flexible trial spacer 10 may be removed and replaced with a different trial spacer 10 until the proper size is found. Alternatively, the proper size flexible interbody spacer 10 may be determined prior to surgery and thus no flexible trial spacer 10 may be needed. A flexible interbody spacer 10 is engaged with the guide rail track 55 at the proximal end 53 and slid along the guide rail instrument 50 along a non-linear insertion path $N_{IP}$ to the desired disc space DS. Hinge sections 12 of the flexible trial spacer 10 allow the spacer 10 to flex as it travels along the non-linear insertion path $N_{IP}$. Flexible spacer 10 is then pushed into the disc space DS until it occupies the space that was originally occupied by patient's disc material. In one embodiment the insertion of flexible spacer 10 into the disc space DS may be facilitated by a sloped nose 24 on the front end 14 of the flexible spacer 10. After the flexible spacer 10 has been placed into its proper position with the disc space DS, the guide rail instrument 50 is disengaged from the adjacent vertebrae V by using the drive mechanism 54 as described above in reference to attaching engagement member 64 but manipulating the drive mechanism in the opposite direction. Guide rail instrument 50 is then removed from the area.

It will be appreciated by those skilled in the art that changes could be made to the embodiments described above without departing from the broad inventive concept thereof. For example, it will be understood that while embodiments have been described in the context of replacing an intervertebral disc this application may have uses involving other interbody spaces. It is understood, therefore, that this invention is not limited to the particular embodiments disclosed, but is intended to cover modifications within the spirit and scope of the present invention as defined by the above description.

What is claimed:

1. An implant system for positioning a flexible spacer between adjacent vertebrae, the implant system comprising:
a flexible interbody spacer including a spacer body that defines a top surface and a bottom surface each configured to engage one of the adjacent vertebrae, opposed side surfaces extending between the top surface and the bottom surface, a lateral axis extending between the opposed side surfaces and substantially parallel to the top and bottom surfaces, and a plurality of hinge sections that permit the interbody spacer to flex about the lateral axis, the interbody spacer defining a height measured from the top surface to the bottom surface at a location between adjacent ones of the plurality of hinge sections, and the interbody spacer defining a width perpendicular to the height, the width measured from one of the opposed side surfaces to the other of the opposed side surfaces at a location between the adjacent ones of the plurality of hinge sections, the width being greater than the height, and the interbody spacer including a mating surface extending along one of the opposed side surfaces, wherein each of the plurality of hinge sections is defined by a notch that extends into the spacer body from the bottom surface and terminates within the spacer body prior to reaching the top surface; and a guide rail including a guide rail body that defines a proximal end, an opposed distal end, an inner surface that faces either the top or bottom surface of the interbody spacer when the interbody spacer is received by the guide rail, the guide rail body further including a track extending between the proximal end and the distal end along a non-linear path, the mating surface slidably engagable with the track to guide the flexible interbody spacer from the proximal end to the distal end along the non-linear path; wherein the inner surface defines a curvature about an axis that is parallel to the lateral axis when the mating surface is slidably engaged with the track.

2. The system of claim 1, wherein the mating surface comprises a groove.

3. The system of claim 1, wherein the mating surface comprises a recess.

4. The system of claim 3, wherein the recess comprises shape selected from the group consisting of slot with round tip, T-shaped, and triangular.

5. The system of claim 1, wherein the track comprises a channel.

6. The system of claim 5, wherein the channel comprises a base member and opposing side walls.

7. The system of claim 1, wherein the hinge sections comprise demineralized bone segments.

8. The system of claim 1, wherein the top surface and the bottom surface comprise a plurality of teeth.

9. The system of claim 1, wherein the flexible interbody spacer further comprises a front end and a back end.

10. The system of claim 9, wherein the front end comprises a sloped nose.

11. The system of claim 1, wherein the flexible spacer comprises a plurality of rigid segments and a spanning member which is inserted through the plurality of rigid segments.

12. The system of claim 1, wherein the guide rail instrument further comprises an engagement mechanism located at the proximal end.

13. The system of claim 12, wherein the engagement mechanism comprises a fastener.

14. The system of claim 12, wherein the guide rail instrument further comprises a drive mechanism, the drive mechanism being operatively connected to the engagement mechanism.

15. The system of claim 1, wherein the notch extends into the spacer body in a direction that is perpendicular to both the axis and the lateral axis.

16. A flexible interbody spacer for positioning between adjacent vertebrae, the flexible spacer comprising:
a top vertebra contacting surface and an opposed bottom vertebra contacting surface each configured to engage one of the adjacent vertebrae, and opposed side surfaces each extending between the top vertebra contacting surface and the bottom vertebra contacting surface, the top vertebra contacting surface spaced from the bottom vertebra contacting surface in a first direction;
a front end and an opposed back end extending between the top and bottom vertebra contacting surfaces, a central axis extending between the front end and the back end, and a lateral axis extending between the opposed side surfaces and perpendicular to the central axis, the spacer defining a length from the front end to the back end along the central axis; and
at least one hinge section positioned between the front end and the back end, each of the at least one hinge sections allowing the spacer to flex about a respective axis that is: 1) perpendicular to the first direction and 2) parallel to the lateral axis;
wherein each of the respective axes is positioned closer to the top vertebra contacting surface than the bottom vertebra contacting surface, each of the at least one hinge sections extends into the flexible spacer from the bottom vertebra contacting surface and terminates within the flexible spacer between the bottom surface and the top vertebra contacting surface, and the flexible spacer is devoid of any hinge sections that allow the flexible spacer to flex about a respective axis that is positioned closer to the bottom vertebra contacting surface than the top vertebra contacting surface.

17. The flexible spacer of claim 16, wherein at least one of the top vertebra contacting surface and the bottom vertebra contacting surface comprises a rough surface.

18. The flexible spacer of claim 17, wherein the rough surface comprises a plurality of teeth.

19. The flexible spacer of claim 16, wherein the front end comprises a sloped nose.

20. The flexible spacer of claim 19, wherein the sloped nose tapers to a rounded tip.

21. The flexible spacer of claim 16, wherein the rear end comprises at least one recess configured to engage with an insertion tool.

22. The flexible spacer of claim 16, wherein each of the at least one hinge sections comprises a notch and each notch has a depth defined as the distance the notch extends into the flexible spacer in the first direction from the bottom vertebra contacting surface toward the top vertebra contacting surface.

23. The flexible spacer of claim 22, wherein the flexible spacer defines a height that is measured from the top vertebra contacting surface to the bottom vertebra contacting surface along a line perpendicular to the central axis, and the notch extends from the bottom vertebra contacting surface through more than half of the height of the flexible spacer toward the top vertebra contacting surface.

24. The flexible spacer of claim 22, wherein the first direction is substantially perpendicular to the central axis.

25. The flexible spacer of claim 22, wherein the notch extends through both of the opposed side surfaces.

26. The flexible spacer of claim 22, wherein the first direction is perpendicular to the lateral axis.

27. The flexible spacer of claim 16, further comprising a mating surface configured to slidably attach to a guide rail instrument.

28. The flexible spacer of claim 27, wherein the mating surface comprises a configuration comprising one of tongue-and-groove, rail-and-slot, dove tail, and various keyed geometries.

29. The flexible spacer of claim 16, wherein the flexible spacer comprises a plurality of rigid segments and the at least one hinge section comprises a spanning member which is inserted through the plurality of rigid segments.

30. The flexible spacer of claim 29, wherein the spanning member comprises material selected from the group consisting of silicone, polyethylene, ultra-high molecular weight polyethylene, braided cable, suture, wire, and braided high-strength fibers.

31. The flexible spacer of claim 29, wherein the spanning member allows the flexible spacer to flex or rotate along the central axis of the flexible spacer.

32. The flexible spacer of claim 16, wherein the flexible spacer comprises material selected from the group consisting of polyether-ether-ketone (PEEK), porous PEEK, titanium, titanium alloys, metal alloys, foamed metal alloys, sintered metal alloys, ceramics, and sintered ceramics.

33. The flexible spacer of claim 16, wherein the flexible spacer comprises allograft bone.

34. The flexible spacer of claim 33, wherein the at least one hinge section comprises demineralized allograft bone allowing the flexible spacer to rotate or flex along the central axis.

35. The flexible spacer of claim 34, wherein the demineralized allograft bone is manufactured by a process selected from the group consisting of surface masking, necking, and drilling holes in a region to be demineralized.

36. The flexible spacer of claim 33, wherein the flexible spacer comprises a plurality of rigid segments made of allograft bone and the at least one hinge section comprises a spanning member made of allograft tendon which is inserted through the plurality of rigid segments.

37. The flexible spacer of claim 36, wherein the allograft tendon comprises material selected from the group consisting of Achilles tendon allograft, bone-patellar tendon-bone allografts, and fascia lata allografts.

38. The flexible spacer of claim 16, wherein the distance between the top vertebra contacting surface and the bottom vertebra contacting surface along a line perpendicular to the central axis defines a height.

39. The flexible spacer of claim 38 wherein the height of the spacer varies along the central axis of the spacer.

40. The flexible spacer of claim 38, wherein the height of the spacer at the rear end is greater than the height of the spacer at the front end.

41. A guide rail instrument configured to position a flexible spacer between adjacent vertebrae, the guide rail instrument comprising:
a guide rail body portion defining a proximal end and a distal end opposite the proximal end, the guide rail body portion having a non-linear shape so as to define a non-linear delivery path between the proximal and distal ends, the guide rail body portion further defining a track that extends between the proximal and distal ends along the non-linear delivery path, the track including a first end and a second end opposite the first end, wherein the flexible spacer enters the track at the first end, travels in a direction along the non-linear delivery path, and exits the track at the second end, the track configured to engage a corresponding mating surface of the flexible vertebral spacer, so as to allow the spacer to travel from the first end to the second end; and
an engagement mechanism including an engagement member that extends beyond both the distal end of the guide rail body and the second end of the track with respect to the direction, a drive mechanism opposite the engagement mechanism, and a drive body operably connecting the engagement member to the drive mechanism such that the drive body is configured to transfer a rotational force that is applied to the drive mechanism to the engagement member;
wherein the engagement member is configured to be driven through an exterior surface of one of the vertebrae such that the guide rail instrument is secured relative to the one of the vertebrae prior to insertion of the spacer between the adjacent vertebrae.

42. The rail instrument of claim 41, wherein the body portion has a substantially rectangular cross-section sized to deliver the flexible spacer between the adjacent vertebrae.

43. The rail instrument of claim 41, wherein the body portion has a substantially "C-shaped" cross-section.

44. The rail instrument of claim 41, wherein the track comprises a lip configured to slidably engage with corresponding grooves of the flexible spacer.

45. The rail instrument of claim 41, wherein the track comprises a configuration of tongue-and-groove, rail-and-slot, dove tail, or various keyed geometries.

46. The rail instrument of claim 41, wherein the mating surface is additionally configured to engage with a tissue retractor or a discectomy and endplate preparation instrument and deliver the tissue retractor or preparation instrument along a non-linear delivery path to a disc space.

47. The rail instrument of claim 41, wherein the engagement mechanism comprises a fastener.

48. The rail instrument of claim 41, wherein the direction is a first direction, and the drive mechanism extends beyond the proximal end with respect to a second direction that is opposite the first direction.

49. A kit for positioning a flexible spacer between adjacent vertebrae, the kit comprising:
a plurality of flexible interbody spacers, each of the plurality of flexible spacers comprising: a spacer body including:
a top surface configured to engage one of the adjacent vertebrae, a bottom surface configured to engage another of the adjacent vertebrae, and opposed side surfaces extending between the top surface to the bottom surface, a front end, a back end, a central axis extending between the front end and the back end, a lateral axis extending between the opposed side surfaces such that the lateral axis is perpendicular to the central axis, a length measured from the front end to the back end along the central axis, and a height measured from the top surface to the bottom surface; a mating surface configured to slidably attach to corresponding surface on a guide rail instrument mating surface; and
at least one hinge section spaced along the length, each of the hinge sections allowing the spacer body to flex about the lateral axis, wherein each of the plurality of hinge sections is defined by a notch that extends into the spacer body from the bottom surface and terminates within the spacer body prior to reaching the top surface; and a guide rail instrument comprising:
a body portion having a non-linear shape, the body portion also comprising a distal end and a proximal end;
an engagement mechanism located at the distal end; and
the guide rail track configured to engage the flexible spacer mating surface on the plurality of flexible spacers.

50. The kit of claim 49, wherein the plurality of flexible spacers include spacer bodies of various sizes and shapes.

51. The kit of claim 49, wherein the engagement mechanism comprises a fastener.

52. The kit of claim 49, wherein the guide rail instrument further comprises a drive mechanism located at the proximal end and operatively connected to the engagement mechanism.

53. The kit of claim 49, wherein the flexible spacer mating surface and the guide rail mating surface comprise a configuration of tongue-and-groove, rail-and-slot, dove tail, or various keyed geometries.

54. The kit of claim 49, wherein the notch extends into spacer body in a direction that is perpendicular to both the central axis and the lateral axis.

* * * * *